United States Patent [19]

Brunelle et al.

[11] 4,349,486

[45] Sep. 14, 1982

[54] MONOCARBONATE TRANSESTERIFICATION PROCESS

[75] Inventors: Daniel J. Brunelle, Scotia; William E. Smith, Schenectady, both of N.Y.

[73] Assignee: General Electric Company, Schenectady, N.Y.

[21] Appl. No.: 202,571

[22] Filed: Oct. 31, 1980

Related U.S. Application Data

[63] Continuation-in-part of Ser. No. 969,683, Dec. 13, 1978, abandoned.

[51] Int. Cl.$^3$ ............................................. C07C 68/06
[52] U.S. Cl. ..................................................... 260/463
[58] Field of Search ........................................ 260/463

[56] References Cited

U.S. PATENT DOCUMENTS

| | | | |
|---|---|---|---|
| 2,787,632 | 4/1957 | Stevens | 260/463 |
| 2,915,529 | 12/1959 | Bell et al. | 260/463 |
| 3,625,920 | 12/1971 | Borkowski | 260/463 |
| 3,642,858 | 2/1972 | Frevel et al. | 260/463 |
| 4,005,121 | 1/1977 | Senet | 260/463 |
| 4,062,884 | 12/1977 | Romano et al. | 260/463 |

FOREIGN PATENT DOCUMENTS 2615665 10/1976 Fed. Rep. of Germany ...... 260/463

OTHER PUBLICATIONS

Thielheimer; Synthetic Methods, vol. 26:219, (1972), vol. 25:127, (1971), vol. 18:259, (1964).

*Primary Examiner*—Mary C. Lee
*Attorney, Agent, or Firm*—Peter A. Bielinski; James C. Davis, Jr.; Joseph T. Cohen

[57] ABSTRACT

A monocarbonate transesterification process comprising contacting in the presence of a base, a beta-fluoroaliphatic carbonate and a compound selected from the class consisting of monohydroxy aliphatic alcohols, phenols and ortho-positioned dihydroxy aromatic compounds. The resulting monocarbonates are useful as monocarbonates, per se, or useful in the preparation of polycarbonates which can be molded or formed into films, laminates or reinforced plastics by conventional techniques.

10 Claims, No Drawings

MONOCARBONATE TRANSESTERIFICATION PROCESS

This application is a continuation in part of application Ser. No. 969,683, filed Dec. 13, 1978, now abandoned.

CROSS REFERENCE TO RELATED APPLICATIONS

This invention is related to copending U.S. patent application Ser. No. 969,682 of J. E. Hallgren and W. E. Smith and U.S. Pat. No. 4,217,438, Ser. No. 970,058, of D. J. Brunelle and W. E. Smith, both filed on Dec. 15, 1978. The aforesaid applications are assigned to the same assignee as the assignee of this application and all the disclosures contained therein are hereby incorporated herein in their entirety by reference.

BACKGROUND OF THE INVENTION

1. Field of Invention

This invention relates to a monocarbonate process comprising contacting in the presence of a base, a beta-fluoroaliphatic carbonate and a monofunctional hydroxy compound selected from alcohols and phenols.

2. Description of the Prior Art

In general, the prior art including "Encyclopedia of Polymer Science and Technology", Vol. 10, (1969) and "Chemistry and Physics of Polycarbonates", Polymer Reviews, H. Schnell, Vol. 9, John Wiley and Sons, Inc. (1964) reports that transesterification of aliphatic hydroxy compounds with carbonic acid aliphatic or aromatic diesters occurs readily in the presence of a basic catalyst and is a convenient method of synthesis of higher carbonates. Heretofore, to the best of our knowledge, the efficient transesterification of a monofunctional phenol with a carbonic acid aliphatic diester in the substantial absence of undesirable side reactions has not been reported.

Unaccountably and nonanalogous with the practice of this invention—wherein transesterification of a monofunctional phenol with a carbonic acid beta-fluoroaliphatic diester occurs, transesterification with a chloroaliphatic diester does not occur.

Further, unexpectedly, when a phenolic reactant and a bis(beta-fluoroaliphatic) carbonate, also commonly referred to as a carbonic acid aliphatic diester, is contacted in the presence of a base, ester interchange (also commonly referred to as re-, trans- or interesterification) occurs resulting in the formation of an aromatic carbonate and a beta-fluoroaliphatic alcohol. Generally and further, unexpectedly, only small amounts of carbonic acid aliphatic-aromatic mixed diester is associated with the isolated aromatic monocarbonate reaction product.

DESCRIPTION OF THE INVENTION

This invention embodies a monocarbonate transesterification process comprising contacting in the presence of a base, a beta-fluoroaliphatic carbonate, and a compound selected from the class of monohydroxy aliphatic alcohols, monohydroxy phenols and ortho-positioned dihydroxy aromatic compounds. The process reactants and the resulting reaction products are illustrated by Equation (I) which follows:

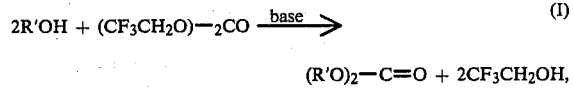

$$2R'OH + (CF_3CH_2O)_2CO \xrightarrow{base} (R'O)_2-C=O + 2CF_3CH_2OH, \quad (I)$$

wherein R' is an alkyl, a cycloalkyl, or an aryl radical.

A "monohydroxy aliphatic alcohol" is defined herein and in the appended claims as any monohydroxy-substituted aliphatic including cycloaliphatic alcohol. Illustratively, a monohydroxy aliphatic alcohol is described by the formula

$$R_a(OH) \quad (II)$$

where $R_a$ represents an aliphatic radical having a single —OH radical is attached directly to an aliphatic or cycloaliphatic carbon atom. Where used herein both in the specification and in the claims the term "radical" is used interchangeably with the expression "group". The alcohol can be any aliphatic alcohol including primary, secondary, or tertiary alcohols, also including —but not limited thereto—carbo-monocyclic, carbo-polycyclic or fused carbo-polycyclic alcohol systems which are connected to each other by single or double valence bonds or bi- or multi-valent radicals.

Illustrative of monohydroxy aliphatic alcohols are methanol; ethanol; 1-propanol; 2-propanol; allyl alcohol; 1-butanol; 2-methyl-1-propanol (isobutyl alcohol); crotyl alcohol; 1-hexanol; cyclohexanol; benzyl alcohol; cyclohexyl carbinol; 1-octanol; 2-ethyl-1-hexanol; isooctyl alcohol; 1-decanol; isotridecyl alcohol; 1-octadecanol (stearyl alcohol); triphenyl carbinol, etc.

A "monohydroxy phenol" is defined herein and in the appended claims as "any monohydroxy-substituted aromatic compound". Illustratively, a monohydroxy phenol is described by the formula:

$$R_b(OH) \quad (III)$$

wherein $R_b$ represents an aromatic radical having a single —OH radical attached directly to an aromatic ring carbon atom.

The $R_b$ aromatic radical can be carbo-monocyclic, carbo-polycyclic, or fused carbo-polycyclic, and can have two or more cyclic systems (monocyclic, polycyclic, or fused polycyclic systems) which are connected to each other by single or double valence bonds or bi- or multi-valent radicals.

Illustrative of monohydroxy phenols are phenol itself (hydroxy benzene); o-cresol; m-cresol; p-cresol; o-chlorophenol; m-chlorophenol; p-chlorophenol; p-bromophenol; 2,4,6-trichlorophenol; 2,4,6-tribromophenol; o-nitrophenol; m-nitrophenol; p-nitrophenol; 2,4-dinitrophenol; guaiacol; anol; eugenol; isoeugenol; saligenin; carvacrol; thymol; o-hydroxyacetophenone; p-hydroxyacetophenone; o-hydroxydiphenyl; p-hydroxydiphenyl; o-cyclohexylphenol, p-cyclohexylphenol, etc.

An "ortho-positioned dihydroxy aromatic compound" is defined herein and in the appended claims as any dihydroxy substituted aromatic compound having two hydroxy groups ortho-positioned relative to each other, i.e. attached to adjacent carbon atoms of the same aromatic ring. Illustratively, the ortho-positioned dihydroxy substituted aromatic compounds can be described by the formula $R_c(OH)_n$, wherein $R_c$ represents an aromatic radical having at least two —OH radicals ortho-positioned relative to each other, each hydroxyl group being directly attached to adjacent aromatic ring carbon atoms, n being a number at least equal to 2. The $R_c$ radical can be carbo-monocyclic, carbo-polycyclic, or fused carbo-polycyclic, and can have two or more cyclic systems (monocyclic, polycyclic or fused polycyclic systems) connected to each other by single or double valence bonds, or bi- or multi-valent radicals.

Illustrative of ortho-positioned dihydroxy aromatic compounds are catechol, i.e. 1,2-dihydroxy benzene; 1,2-dihydroxy naphthalene; pyrogallol, i.e. 1,2,3-trihydroxybenzene; 1,2-dihydroxydiphenyl; 1,2-dihydroxyanthracene; etc.

Any beta-fluoroaliphatic carbonate can be used in our process and is defined herein in the appended claims as a "beta-fluoroaliphatic carbonate". Illustratively, the beta-fluoroaliphatic carbonate reactant can be described by the generic formula:

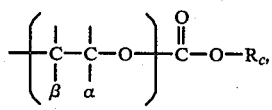
(V)

which describes the essential features of a beta-fluoroaliphatic carbonate reactant i.e., a carbonate class wherein at least two oxy groups are both independently and directly bonded to the same carbonyl carbon atom subject to the proviso that at least one of the oxy groups is separated from at least one fluorine atom by at least two aliphatic carbon atoms, $R_c$, optionally, being a

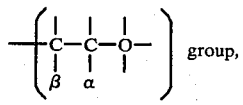 group, or an alkyl, a cycloalkyl, or aryl radical, including combinations thereof.

Further, illustratively the beta-fluoroaliphatic carbonates can be saturated, unsaturated, linear or branched, etc., in skeletal form. Further the beta-fluoroaliphatic carbonates can be carbo-monocyclic, carbo-polycyclic or fused carbo-polycyclic and can have two or more cyclic systems (monocyclic, polycyclic or fused polycyclic systems) which are connected to each other by single or double valence bonds or bi- or multivalent radicals.

The above described class of beta-fluoroaliphatic carbonate reactants can be prepared by the reaction of any beta-fluoroaliphatic or cycloaliphatic alcohol with phosgene in accordance with the method described by Aldrich and Shepherd in the "Journal of Organic Chemistry", Vol. 29, pages 11–15 (1964), or by the reaction of an aliphatic or cycloaliphatic beta-fluoroalcohol, carbon monoxide, and a Group VIIIB element selected from ruthenium, rhodium, palladium, osmium, iridium or platinum as described in J. E. Hallgren et al., in U.S. Ser. No. 969,682, filed Dec. 15, 1978.

Illustrative of commercially available beta-fluoroaliphatic alcohols that can be used as precursors of beta-fluoroaliphatic carbonates are the following:

CF$_3$CH$_2$OH,
(CF$_3$)$_2$CH$_2$OH,
CF$_3$CF$_2$CH$_2$OH,

-continued

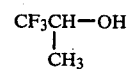

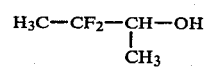

CF$_3$CF$_2$CF$_2$CH$_2$OH, and
(CF$_3$)$_3$COH.

Methods for the preparation of beta-fluoroalcohols are well known, and include, e.g. lithium aluminum hydride reduction of fluorinated esters as described by K. N. Campbell et al. in the "Journal of American Chemical Society", Volume 72, page 4380 (1950) as well as the catalytic reduction of fluorinated esters, e.g. as described in U.S. Pat. Nos. 3,314,987, 3,356,747, and 3,390,191.

Preferred beta-fluoroaliphatic carbonates are bis(-beta-fluoroaliphatic) or bis(beta-fluorocycloaliphatic) carbonate reactants which contain from 4–20, and more preferably contain from 4–10 aliphatic carbon atoms. Bis(beta-fluoroaliphatic) and bis(beta-fluorocycloaliphatic) carbonates include bis(beta-fluoroalkyl) and bis(beta-fluorocycloalkyl) carbonates of the formulas:

(CF$_3$CH$_2$O$)_2$CO,
((CF$_3$)$_2$CH$_2$O$)_2$CO,
(CF$_3$CF$_2$CH$_2$O$)_2$CO,

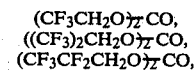

(CF$_3$CF$_2$CF$_2$CH$_2$—O$)_2$CO.

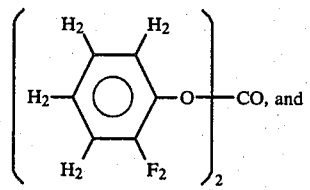

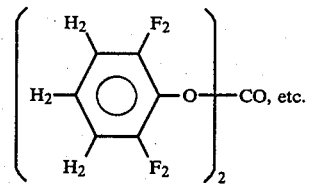

This process can be carried out in the absence of any solvent, e.g. where the alcohol, phenol, etc., and/or beta-fluoroaliphatic carbonate act(s) as both reactant and solvent. The process can also be carried out in the presence of a non-polar or low to medium polar solvent subject to the proviso, more preferably, that the solvent employed be substantially free of protic solvents, especially protic solvents capable of strong hydrogen bonding. In general, among presently preferred solvents are the following:

(A) non- or low-polar solvents such as hexane, 3-methylpentane, heptane, cyclohexane, methylcyclohexane, cyclohexane, isooctane, p-cymene, cumene, decalin, toluene, xylene benzene, diethylether, diphenyl ether, dioxane, thiophene, dimethylsulfide, ethyl acetate, tetrahydrofuran, etc., including mixtures thereof, and (B) medium-polarity solvents such as chlorobenzene, anisol, bromobenzene, dichlorobenzenes, methyl formate, isodobenzene, acetone, acetophenone, etc., including mixtures thereof.

Although not limiting the process of this invention or the scope thereof to any theory, we believe that the process rate is associated with the polarity and dielectric strengths of the solvent employed. It is also believed that a proton-transfer reaction is involved which is significantly effected by the solvent in its initial and transition state. Accordingly, in general, it is believed desirable that the solvent employed be selected from the group consisting of any non-polar or polar solvent class which solvent classes are characterized as classes of solvents substantially free of high dielectric constant values, i.e. solvents incapable of strong hydrogen bonding to phenolic reactants or any intermediates derived therefrom during the course of the reaction. In general, solvents which are preferably excluded from the reaction medium are polar protic solvents characterized as solvent species which have the capability of donating strong hydrogen bonding to solute species and which have high dielectric constants, e.g. dielectric constants of from about 20 to about 50 or even higher. Non- or low-polar solvents are defined herein are characterized in accordance with the solvent polarity scales described in Solute-Solvent Interactions, J. F. Kotese and K. D. Richey (1969) Marcl Dekker, pages 281-282.

In general, the process can be carried out in any basic reaction medium, preferably that provided by the presence of any inorganic or organic base.

Representative of basic species which can be employed are the elemental following: alkali and alkaline earth metals; basic quaternary ammonium, quaternary phosphonium or tertiary sulfonium compounds; alkali or alkaline earth metal hydroxides; salts of strong bases and weak organic acids; primary, secondary or tertiary amines; etc. Specific examples of the aforementioned are sodium, potassium, magnesium metals, etc.; quaternary ammonium hydroxides, tetraethyl phosphonium hydroxides, etc.; sodium, potassium, lithium, and calcium hydroxide; quaternary phosphonium, tertiary sulfonium, sodium, lithium and barium carbonates, sodium acetate, sodium benzoate, sodium methylate, sodium thiosulfate, sodium compounds, e.g. sulfide, tetrasulfide, cyanide, hydride and borohydride; potassium fluoride, methylamine, isopropylamine, methylethylamine, allylethylamine, ditertbutylamine, dicyclohexylamine, dibenzylamine, tert-butylamine, allyldiethylamine, benzyldimethylamine, diacetylchlorobenzylamine, dimethylphenethylamine, 1-dimethylamino-2-phenylpropane, propanediamine, ethylenediamine, N-methylethylenediamine, N,N'-dimethylethylenediamine, N,N,N'-tritert-butylpropanediamine, N,N',N',N''-tetramethyldiethylenetriamine, pyridine, aminomethylpyridines, pyrrole, pyrrolidine, piperidine, 2,2,6,6-N-pentamethylpiperidine, imidazole, etc. Especially preferred bases are the hydroxides of lithium, sodium, potassium, calcium or barium; sodium, lithium or barium carbonate, sodium acetate, sodium benzoate, sodium methylate, lithium, sodium or potassium, etc., phenoxide; lithium, sodium or potassium, etc., salts of phenols; 2,2,2-trifluoroethoxide, beta-trifluoroethanol, etc., including mixtures thereof.

Any amount of base can be employed. In general, effective mole ratios of base to monofunctional hydroxy compounds are within the range of from about $10^{-6}$ to 1 or even lower to about 1 to 1, or even higher, preferably from $10^{-4}$ to 1 to about 0.02 to 1, and more preferably from $10^{-3}$ to 1 to 0.01 to 1. Generally, mole ratios of at least $10^{-3}$ to 1 enhances both the reaction rate and the yield of monocarbonates.

Any reaction pressure can be employed, e.g. atmospheric, subatmospheric or superatmospheric. Generally, however, in the preparation of monocarbonates, the process is preferably carried out under a reaction pressure of approximately 1 atm. (~760 mm. Hg.) during the initial phase of the reaction with a subsequent pressure reduction to values in the order of 50 to 100 mm. Hg. (vacuum), or even lower.

Any reaction temperature can be employed. Optimum reaction temperatures are generally within the range of from 80° C. or even lower, to 300° C. or even higher, and more often 120° C. to 200° C.

Any reaction time can be employed. Generally, optimum reaction time periods are from about 0.5 hours or even less to about 24 hours or even more.

Any amount of solvent can be employed. In general, optimum solvent to monofunctional hydroxy compound mole proportions are from 0 to 10, preferably from 0 to 1.

In order that those skilled in the art may better understand my invention, the following examples are given which are illustrative of the best mode of this invention, however, these examples are not intended to limit the invention in any manner whatsoever. In the examples, unless otherwise specified all parts are by weight and the reaction products were verified by spectroscopic techniques and/or comparison with authentic materials.

EXAMPLE I

Procedure for the preparation of bis(2,2,2-trifluoroethyl) carbonate which is not an example of this invention.

Phosgene gas was bubbled into a 500 ml. 3-neck flask containing 300 ml. of dry ether at 0° C. until 25 g. (0.25 mole) had been added. To this solution at 0° C. was added a solution of 50 g. (0.5 mole) of 2,2,2-trifluoroethanol and 40.3 ml. (0.5 mole) of pyridine in 100 ml. of ether. The addition was carried out over 3 hrs., forming a thick white precipitate. The reaction was then warmed to room temperature and was stirred for one hour. The precipitate was removed by suction filtration and washed with ether. The ether was removed by distillation, and the product was distilled (b.p.=58°/70 mm.; 113°/760 mm.) to yield 49.5 g. (88%) of bis(2,2,2-trifluoroethyl) carbonate.

EXAMPLE II

A 25 ml. flask was charged with 1.37 g. (6 mmol.) of bis(2,2,2-trifluoroethyl) carbonate, 940 mg. (10 mmol.) of phenol, and 2.7 mg. (0.05 mmol.) of sodium methoxide. The mixture was stirred in 10 ml. of solvent, i.e. heptane, while heating to the boiling point of the solvent. The solvent was slowly distilled (over 2 hrs.) removing the coproduct 2,2,2-trifluoroethanol. The residue was cooled and purified by passing through a short column of silica gel. The aromatic diphenyl carbonate (eluted first) was obtained in pure form simply by rotoevaporation. Recovered phenol (eluted second) was similarly obtained. Diphenyl carbonate was isolated in 85% yield (905 mg.); phenol (122 mg. 13%) was also recovered.

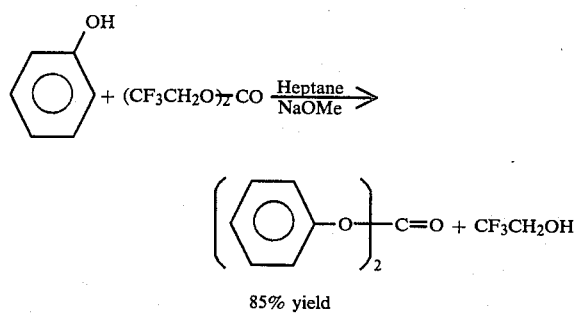

85% yield

EXAMPLE III p-Cumylphenol (2.12 g.; 10 mmol.) was reacted with bis(2,2,2-trifluoroethyl) carbonate (1.37 g.; 6 mmol.) and sodium methoxide (2.7 mg.; 0.05 mmol.) in toluene according to the procedure of Example II. Bis(p-cumylphenyl) carbonate was isolated in 94% yield (2.132 g.), along with the phenol (113 mg., 5%).

94% yield

EXAMPLE IV p-Cresol (1.081 g.; 10 mmol.) was reacted with bis(2,2,2-trifluoroethyl) carbonate (1.37 g.; 6 mmol.) and sodium methoxide (2.7 mg.; 0.05 mmol.) in toluene, according to the general procedure of Example II. Bis(p-cresyl) carbonate was isolated by column chromatography in 70% yield (1.695 g.), along with unreacted p-cresol (0.310 g., 28%).

70% yield

EXAMPLE V 1,2-Catechol (550 mg.; 5.0 mmol.) was reacted with bis(2,2,2-trifluoroethyl) carbonate (1.37 g.; 6 mmol.) and sodium methoxide (2.7 mg.; 0.05 mmol.) in isooctane, according to the procedure of Example II. Catechol carbonate was isolated by dissolution of the product in 1:1 benzene/petroleum ether and filtration, yielding 573 mg. (85%) of the desired carbonate.

85% yield

EXAMPLE VI 1,2-cyclohexanediol (1.16 g.; 10.0 mmol.) was reacted with bis(2,2,2-trifluoroethyl) carbonate (2.26 g.; 10.0 mmol.) and sodium methoxide (2.7 mg.; 0.05 mmol.) in toluene, according to the procedure of Example II. Vpc and thin layer chromatographic (tlc) analysis of the product indicated 97% formation to the desired carbonate, with only a trace of 1,2-cyclohexanediol remaining.

97% yield

EXAMPLE VII

Benzyl alcohol (2.16 g,; 20 mmol.) was reacted with bis(2,2,2-trifluoroethyl) carbonate (2.38 g., 10.5 mmol.) and sodium methoxide (5.4 mg., 0.10 mmol.) in toluene, according to the procedure of Example II. Vpc and tlc analysis indicated clear formation of dibenzyl carbonate and total absence of benzyl alcohol. Isolation by evaporation of solvents gave a quantitative yield of product, which was further characterized by spectral analysis.

100% yield

EXAMPLE VIII n-Hexanol (2.05 g., 20 mmol.) was reacted with bis(2,2,2-trifluoroethyl) carbonate (2.38 g., 10.5 mmol.) and sodium methoxide (5.4 mg., 0.10 mmol.) in 10 ml. of toluene, according to the procedure of Example II. Vpc analysis of the product showed clean formation of di-n-hexyl carbonate. No n-hexanol remained. Isolation of the product by evaporation of solvents gave a quantitative yield of the product, further characterized by spectral analysis.

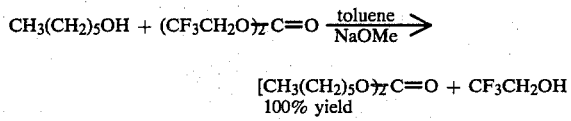

[CH$_3$(CH$_2$)$_5$O]$_2$C=O + CF$_3$CH$_2$OH
100% yield

EXAMPLE IX

A 50-ml. flask was charged with bisphenol-A (2.28 g., 10.0 mmol.), i.e. bis(4-hydroxyphenyl)-propane-2,2—also commonly abbreviated as "BPA", bis(2,2,2-trifluoroethyl) carbonate (4.56 g., 20 mmol.), sodium methoxide (2.5 mg., 0.05 mmol.), and 20 ml. of toluene. The reaction was heated at 120° C. distilling off CF$_3$CH$_2$OH, while following the reaction by tlc. The reaction was terminated when the yield of monocarbonate was highest. Preparative high pressure liquid chromatography yielded 1.98 g. (58%) of the monocarbonate identified by spectral and elemental analysis as 2-(4-hydroxyphenyl)-2-[4-(2,2,2-trifluoroethylcarbonyldioxy)phenyl]propane of the formula

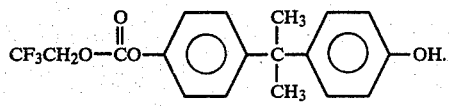

EXAMPLES X–XVI

The effects of solvent on the process of this invention are shown in Table I. Yields shown in Table I are % conversion.

TABLE I

Effect of Solvent on Formation of Diphenyl Carbonate from Phenol and bis(2,2,2-Trifluoroethyl) Carbonate

| Example No. | Solvent | Temp. | Time | % Yield |
| --- | --- | --- | --- | --- |
| X | Heptane | 100° | 2 hr. | 85 |
| XI | Toluene | 125° | 2 hr. | 81 |
| XII | Isooctane | 110° | 2 hr. | 83 |
| XIII | Cyclohexane | 90° | 3 hr. | 70 |
| XIV | Tetrahydrofuran | 70° | 3 hr. | 45 |
| XV | Acetonitrile | 90° | 3 hr. | 40 |
| XVI | n-Propanol | 120° | 1 hr. | 0 |

An efficient feature of the process of this invention is that the relative proportions of aliphatic-aromatic mixed monocarbonates to aromatic carbonates is quite low, i.e., even when excess bis(trifluoroaliphatic) carbonates are employed in reactions involving only monohydroxy substituted aromatic reactants, i.e. the primary product is an aromatic carbonate as opposed to trifluoroaliphatic-aromatic mixed carbonates. The implication of this result is manifest. Only minor proportions of aromatic-aliphatic mixed carbonates are formed, i.e., the reaction is highly selective and efficient in the formation of aromatic carbonates.

The transesterification process described herein is advantageously employed in the preparation of aromatic monocarbonates since the process is highly selective and efficient in the product of aromatic monocarbonates in the substantial absence of deleterious side reactions, e.g. the formation of small amounts of carbonic acid aliphatic-aromatic mixed diester.

In the presently preferred embodiment, the process is carried out by reacting a highly volatile lower temperature boiling beta-fluoroaliphatic carbonate with an aromatic reactant under reaction conditions wherein beta-fluoroalcohols are readily removed from the reaction environment, i.e. evaporation or vaporization continuously as the monocarbonate process is carried to completion.

Further, as generally described by Equation 1, set out herein, the process is broadly applicable in the preparation of aliphatic, cycloaliphatic and aromatic monocarbonates including combinations thereof based on reaction mixtures containing both and various aromatic and/or aliphatic hydroxy compounds.

Although the above examples have illustrated various modifications and changes that can be made in carrying out our process, it will be apparent to those skilled in the art that other changes and modifications can be made in the particular embodiments of the invention described which are within the full intended scope of the invention as defined by the appended claims.

We claim:

1. A monocarbonate transesterification process comprising reacting, in the presence of a base;
(A) a beta-fluoroaliphatic carbonate which is saturated, unsaturated, linear or branched compound of the formula,

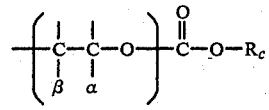

where R$_c$ is selected from the class of a group of the formula,

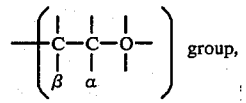

an alkyl radical, a cycloalkyl, aryl radical and combinations thereof which can be carbo-monocyclic, carbo-polycyclic or fused carbo-polycyclic and can have two or more cyclic systems which are connected to each other by a single or double valence bonds or bi- or multi-valent radicals, with
(B) a compound selected from the class consisting of
(1) monohydroxy aliphatic alcohols of the formula, ROH where R$^1$ represents an aliphatic radical or cycloaliphatic radical having a single —OH radical attached directly to the aliphatic or cycloaliphatic carbon atom where the alcohol can be a primary, secondary or tertiary alcohol including carbo-monocyclic, carbo-polycyclic or fused carbo-polycyclic alcohol systems which are connected to each other by single or double valence bonds or bi- or multi-valent radicals;
(2) monohydroxy phenol ROH wherein $R_b$ represents an aryl radical having a single —OH radical attached directly to an aryl ring carbon atom wherein the aryl radical can be carbo-monocyclic, carbo-polycyclic, or fused carbo-polycyclic, and can have two or more cyclic systems which are connected to each other by single or double valence bonds or bi- or multi-valent radicals; and (3) an ortho-positioned dihydroxy aromatic compound of the formula, $$R_c(OH)_n$$

wherein $R_c$ represents an aromatic radical having at least two —OH radicals ortho-positioned relative to each other, each hydroxy group being directly attached to adjacent aromatic ring carbon atoms, n being a number at least equal to 2 wherein the $R_c$ radical can be carbo-monocyclic, carbo-polycyclic, and can have two or more cyclic systems connected to each other by single or double valence bonds, or bi- or multi-valent radicals.

2. The process of claim 1 wherein the alcohol is of the formula R'OH and R' is an alkyl radical.

3. The process of claim 1 wherein the alcohol is of the formula R'OH and R' is an aryl radical.

4. A monocarbonate transesterification process comprising contacting in the presence of a base, a bis(beta-fluoroaliphatic) carbonate selected from the class consisting of the formulas $$(CF_3CH_2O)_2CO,$$
$$((CF_3)_2CH_2O)_2CO,$$
$$(CF_3CF_2CH_2O)_2CO,$$

$$\left( \begin{array}{c} CF_3CH-O \\ | \\ CH_3 \end{array} \right)_2 CO,$$

$$(CF_3CF_2CF_2CH_2-O)_2CO,$$

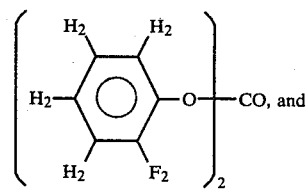

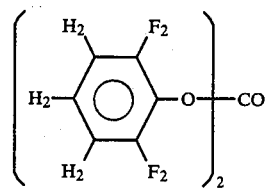

a monohydroxy-substituted aliphatic or aromatic compound of the formula $$R_b(OH)$$

where $R_b$ is selected from the class consisting of alkyl, cycloalkyl and aryl radicals.

5. The process of claim 4 wherein $R_b$ is an $C_{6-10}$ aryl radical.

6. The process of claim 4 wherein $R_b$ is a $C_{1-10}$ alkyl or $C_{6-10}$ cycloalkyl radical.

7. The process of claim 4 further comprising a solvent.

8. The process of claim 7 wherein the solvent is a non-, low-, or medium-polar solvent.

9. The process of claim 8 further comprising separating and recovering a resulting non-fluorinated monocarbonate transesterification reaction product.

10. The process of claim 5 wherein the monocarbonate transesterification reaction product is diphenyl carbonate.

* * * * *